United States Patent [19]

Wong

[11] Patent Number: 5,041,600

[45] Date of Patent: Aug. 20, 1991

[54] BISPHENOL ETHERS

[75] Inventor: Pui K. Wong, Katy, Tex.

[73] Assignee: Shell Oil Company, Houston, Tex.

[21] Appl. No.: 471,464

[22] Filed: Jan. 29, 1990

[51] Int. Cl.$^5$ .......................... C07C 317/22
[52] U.S. Cl. .................. 558/268; 558/271; 568/29; 568/31; 568/33
[58] Field of Search .............. 568/29, 31, 33; 558/268, 271

[56] References Cited

U.S. PATENT DOCUMENTS 4,540,763  9/1985  Kirchhoff .................. 526/281

FOREIGN PATENT DOCUMENTS 3619058  12/1987  Fed. Rep. of Germany ...... 558/268
54-98740  8/1979  Japan .................. 558/268
63-02969  1/1988  Japan .................. 568/33

Primary Examiner—Mary E. Ceperley

[57] ABSTRACT

Arylcyclobutenealkyl diethers of oligomers containing a plurality of aromatic rings at least two of which are joined by a sulfone moiety, are self-curing at temperatures above about 150° C. The cured products exhibit good properties of strength and toughness.

5 Claims, No Drawings

BISPHENOL ETHERS

FIELD OF THE INVENTION

This invention relates to ether derivatives of bisphenolic oligomers having a plurality of aromatic rings, at least two of which are joined by a sulfone moiety. More particularly, the invention relates to arylcyclobutenealkyl ethers of such bisphenolic compounds, to a process for the production thereof and to cured compositions produced from the ethers.

BACKGROUND OF THE INVENTION

The curing of monomeric materials to produce polymeric thermoset resins is well known in the art. In general, the polymerizable monomers have at least one and customarily more than one reactive group which serves as an active site for a curing or crosslinking polymerization to produce the thermoset resins. However, the crosslinking of many if not most polymerizable monomers, for example the curing of epoxy resins, requires the use of a curing agent, catalytic or stoichiometric, to cause the curing or crosslinking to occur at an acceptable rate. Even in the presence of most curing agents the rate of crosslinking is slower than desired and the addition of an accelerator is required to obtain sufficiently rapid curing. Some monomers will cure at an acceptable rate in the absence of a curing agent, but only upon the addition of high intensity energy, e.g., ultraviolet (UV) light.

There are other monomers wherein the active site is such that no additional curing agent or high intensity energy is required and the monomers will cure upon the application of heat. Such monomers are termed "self-curing". One class of such self-curing monomers include within the molecular structure moieties of an arylcyclobutene, e.g., a benzocyclobutene. Without wishing to be bound by any particular theory, it appears likely that upon application of heat the cyclobutene ring undergoes ring-opening to produce active intermediates which crosslink by oligomerization and other reactions with adjacent molecules.

A series of patents to Kirchhoff, illustrated by U.S. Pat. No. 4,540,763, describes the production and curing of a large number of benzocyclobutene derivatives including ethers of di(hydroxyphenyl) compounds such as di(hydroxyphenyl)alkanes, also termed bisphenol alkanes, wherein an ether oxygen directly links a phenyl ring of the di(hydroxyphenyl) compound to the six-membered ring of the benzocyclobutene group. The monomers of Kirchhoff are characterized by this direct link of a functional group to the six-membered ring. The monomers are said to be self-curing. A copending patent application, Ser. No. 349,547, filed May 9, 1989, now U.S. Pat. No. 4,978,721 relates to certain ester derivatives of polymeric materials wherein a pendant carboxy function of the polymer is connected to a arylcyclobutene moiety through an alkylene group. U.S. Pat. No. 4,943,665, is directed to similar ether derivatives of di(hydroxyphenyl) compounds where the ether oxygen is connected to the arylcyclobutene group through an alkylene group. It would be of advantage to provide additional arylcyclobutenealkyl ethers which self-cure upon application of heat to produce thermoset resins having good properties.

SUMMARY OF THE INVENTION

The present invention provides a class of novel ether derivatives of sulfone-containing di(hydroxyphenyl) compounds, a method for the production of such ether compounds and the thermoset resins resulting from the self-curing of the resins. More particularly, the invention relates to arylcyclobutenealkyl ethers of sulfone-containing di(hydroxyphenyl) oligomers.

DESCRIPTION OF THE INVENTION

The novel ethers of the invention are arylcyclobutenealkyl ethers wherein the ether oxygens connect phenyl rings of a sulfone-containing di(hydroxyphenyl) oligomer through an alkylene group attached to a carbon atom of a six-membered ring of an arylcyclobutene group. The sulfur-containing di(hydroxyphenyl) compounds are oligomers derived from di(hydroxyphenyl) compounds and a diphenyl sulfone. The sulfone-containing di(hydroxyphenyl) oligomers are illustratively produced from an excess of a di(hydroxyphenyl) compound and a di(halophenyl) sulfone.

The arylcyclobutenealkyl compounds which are employed as precursors of the ethers of the invention are represented by the formula $$Ar-R-W \qquad (I)$$

wherein Ar is an arylcyclobutene group, R is alkylene of up to 4 carbon atoms and W is an electron-withdrawing group.

Suitable W groups in the above formula I are those groups commonly referred to as good "leaving groups" in nucleophilic substitution reactions. Preferred W groups are upper halo, i.e., halogens other than fluoro (chloro, bromo or iodo), or sulfonic acid groups such as aryl sulfonate, e.g., tosylate, brosolate or nosylate, alkyl sulfonate, e.g., mesylate, and fluoroalkyl sulfonate, e.g., triflate or nonaflate. Particularly preferred as the W group are the upper halogens, especially chloro. The term "R" of formula I is alkylene of up to 4 carbon atoms, e.g., methylene, 1,2-ethylene or 1,3-butylene, but the preferred R group is methylene.

The arylcyclobutene group Ar is an aromatic ring system of up to 4 aromatic rings and up to 30 carbon atoms, inclusive, which contains at least one cyclobutene ring fused to an aromatic ring. Suitable aromatic ring systems are illustrated by the single or fused aromatic ring system compounds benzene, naphthalene, anthracene and phenanthrene and the directly joined ring system compounds of two or more aromatic rings joined by an alkylene group such as diphenylmethylene and 2,2-diphenylpropane. The preferred aromatic ring system is the single aromatic ring system and the preferred arylcyclobutene moiety is a benzocyclobutene moiety. The Ar group is hydrocarbyl containing only atoms of carbon and hydrogen or is substituted hydrocarbyl containing additional atoms as inert carbon atom substituents such as cyano or middle halo, i.e., chloro or bromo. The preferred Ar group is the benzocyclobutene group.

In a particularly preferred embodiment of the invention, the arylcyclobutenealkyl compound is the halomethylbenzocyclobutene of the formula

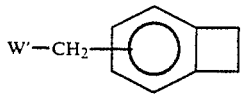

(IA)

wherein W' is upper halo, i.e., chloro, bromo or iodo but preferably chloro. The halomethylbenzocyclobutenes are prepared by one of several reaction schemes depending upon the desired spacial relationship of the halomethyl substituents and the cyclobutene ring. A 4-halomethylbenzocyclobutene is produced from a p-methylbenzyl halide, preferably p-methylbenzyl chloride, in two steps by the procedure of Ewing, et al, J. Chem. Soc., Chem. Comm., 1979, p. 207. Production of 3-chloromethylbenzocyclobutene is effected by a similar procedure starting with o-methylbenzyl chloride. In this case, however, the procedure yields about a 1:2 molar mixture of 3-chloromethylbenzocyclobutene and 4-chloromethylbenzocyclobutene. The mixture is separated into its individual components by conventional methods such as distillation or chromatographic separation or alternatively is used as such without separation of the isomers. Other arylcyclobutenealkyl compounds are known compounds or are produced by known methods.

The sulfone-containing di(hydroxyphenyl) compound is an oligomer having a plurality of aromatic rings at least two of which are connected by a sulfone moiety, i.e., a —SO$_2$—moiety. The oligomers are illustratively produced from a di(halophenyl) sulfone and a molar excess of a di(hydroxyphenyl) compound. As employed herein, the term "oligomer" applies to a low molecular weight material containing as few as one unit of each type of oligomer precursor up to a material of up to about 25 monomeric units or even slightly more. Although a variety of oligomers produced from a variety of di(hydroxyphenyl) compounds are useful in the production of the ethers of the invention, the preferred oligomers are represented by the formula with a di(halophenyl) sulfone of the formula

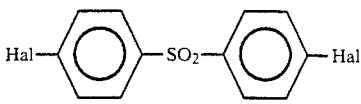

(IV)

The hydroxyphenyl compounds of formula III are known compounds illustrated by di(4-hydroxyphenyl)methane, 2,2-di(4-hydroxyphenyl)propane, di(4-hydroxyphenyl) ether, di(4-hydroxyphenyl) sulfone and di(4-hydroxyphenyl) ketone. Within formula IV, Hal represents halogen, i.e., fluoro, chloro, bromo or iodo. The preferred Hal substituents, however, are chloro.

The oligomers are produced, in the preferred modification, by reaction of a metal salt of the di(hydroxyphenyl) compound (formula III) with the di(halophenyl) sulfone (formula IV). Although a variety of metal salts are useful in the production of the oligomers, the preferred metal salts are alkali metal salts and lithium, sodium, potassium, rubidium and cesium salts are satisfactory. Sodium or potassium salts are preferred. In one variation of the process, the alkali metal salt of the di(hydroxyphenyl) compound is formed and isolated prior to reaction with the di(halophenyl) sulfone. The di(hydroxyphenyl) compound is contacted with strong alkali metal base, e.g., alkali metal hydroxide, in aqueous solution at moderate temperatures from about 15° C. to about 30° C. Subsequent to reaction the alkali metal salt is isolated by conventional methods such as solvent removal or selective extraction. In a preferred variation of the process for oligomer production the alkali metal salt is formed as described above and is reacted in situ with the di(halophenyl) sulfone. Such a reaction is most easily conducted in a mutual solvent such as dimethylsulfoxide at a reaction temperature of from about 150° C. to about 160° C. See, by way of illustration, Chiang et al, Polymer, 1981, 22, 3.

The alkali metal salts produced by the oligomerization process described above are isolated by conven-

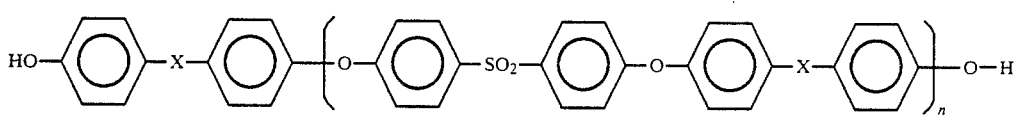

(II)

wherein X independently is a direct valence bond, alkylene of up to 8 carbon atoms inclusive, oxy, thio, sulfonyl, carbonyl or carbonyldioxy and n is an average number from 1 to about 20, preferably from 1 to about 10. Within the oligomers of the above formula II it is preferred that at least one X is alkylene such as methylene or 2,2-propylene and the group of alkylene, oxy and sulfonyl linking groups is a preferred class of X moieties.

The oligomers are known compounds or are produced by known methods. In general, the preferred process for oligomer production comprises the reaction of a metal salt of at least one di(hydroxyphenyl) compound of the formula

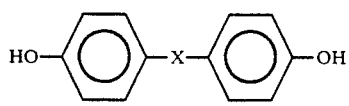

(III)

tional methods and/or converted to the oligomer by acidification. However, in order to produce the arylcyclobutenealkyl ethers of the invention it is convenient and preferred to further react the alkali metal salt of the oligomer with the arylcyclobutene alkyl compound of formula I without separation or isolation of the oligomer intermediate. The reaction of the alkali metal salt of the oligomer and the arylcyclobutenealkyl compound is conducted in what is conventionally termed an interfacial reaction. Reaction takes place at the interface of a solution containing the alkali metal oligomer salt, typically an aqueous solution, and a second solution of the arylcyclobutenealkyl compound in a solvent such as chloroform or chlorobenzene. A phase-transfer agent, typically a quaternary ammonium salt, is provided to facilitate reaction and reaction temperatures are suitably from about 15° C. to about 100° C. The reaction of the oligomer salt and the arylcyclobutenealkyl compound is also conducted in single solvents such as dimethylsulfoxide at somewhat higher reaction temperatures. The resulting arylcyclobutenealkyl ether is isolated by conventional procedures such as extraction, solvent removal or precipitation with a non-solvent.

The ethers, broadly, are conveniently depicted by removal of the hydroxylic hydrogens of the oligomer and the replacement thereof by arylcyclobutenealkyl groups. In terms of the oligomers of formula II and the preferred arylcyclobutenealkyl compounds of formula IA, the oligomers are illustrated by the formula

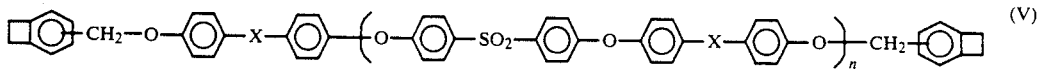 (V)

wherein n and X have the previously stated meanings. The nomenclature of such arylcyclobutenealkyl ethers is difficult because of the complexity thereof but the identity of the ether products will be apparent from consideration of the formulas and description of the precursors of the ethers. Of particular interest are the benzocyclobutenemethyl ethers of oligomers formed from di(4-halophenyl) sulfone and 2,2-di(hydroxyphenyl)-propane of number average molecular weight from about 2000 to about 4000, as determined by gel permeation chromatography or nuclear magnetic resonance analysis.

The arylcyclobutenealkyl ethers are generally solids of moderate glass transition temperatures. The ethers are characterized by stability and a long shelf-life at ambient temperature. The ethers are self-curing or are cured without the necessity of providing accelerators by heating the ether to an elevated temperature, typically above about 150° C. or even above about 200° C. The cured products have relatively high glass transition temperatures, often over 200° C. and are rigid thermosets with good tensile strength. The ethers are processed by conventional methods employed in the curing of monomeric materials to thermoset resins and the cured products find utility in applications such as coatings and structural materials in electronic and aerospace industries.

The invention is further illustrated by the following Illustrative Embodiments which should not be regarded as limitations.

ILLUSTRATIVE EMBODIMENT I

A dihydroxyl-terminated polysulfone oligomer of the type illustrated by formula II wherein n is an average number of about 6 was produced from 2,2-di(4-hydroxyphenyl)propane and di(4-chlorophenyl) sulfone according to the procedure of Chiang et al, Polymer, 1981, 22, 3. To a solution of 90 g of this oligomer and 11.7 g of 4-chloromethylbenzocyclobutene in 500 ml of chlorobenzene was added 13.6 g of sodium hydroxide and 2 g of tetra-n-butylammonium bisulfate in 30 ml of water. This mixture was heated to 80° C. and maintained for 20 hours while being stirred. The resulting organic layer was separated and placed in an operating Waring blender containing isopropanol. The resulting precipitate was washed twice in water in the blender, dissolved in tetrahydrofuran, reprecipitated from isopropanol and dried in vacuo at 100° C. to give 95 g of an off-white product. Gel permeation chromatography and $^1$H-NMR analysis indicated that the product had a number average molecular weight of about 3100.

ILLUSTRATIVE EMBODIMENT II

A crosslinked film approximately 0.025 cm in thickness was produced by compression molding of a sample of the ether of Illustrative Embodiment I. In part because of a relatively low glass transition temperature of 142° C. and a low melt viscosity, the sample was easily molded into a void-free film. When measured by conventional testing methods the modulus (psi) of the film was found to be 282,000 and the tensile strength (psi) was 10,600. Elongation at break was found to be 6.1%.

What is claimed is:

1. An arylcyclobutenealkyl diether of a di(hydroxyphenyl) oligomer of from 6 to 82 aromatic rings at least two of which are connected by a sulfone moiety with the remainder being connected by direct valence bond, alkylene of up to 8 carbon atoms inclusive, oxy, thio, sulfonyl, carbonyl or carbonyldioxy.

2. The diether of the formula

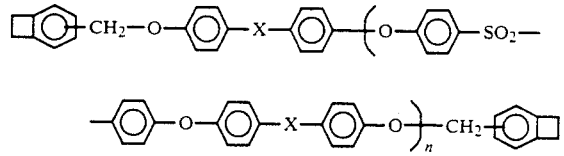

wherein X independently is a direct valence bond, alkylene of up to 8 carbon atoms inclusive, oxy, thio, sulfonyl, carbonyl or carbonyldioxy, and n is an average number from 1 to about 20.

3. The diether of claim 2 wherein X is alkylene, oxy or sulfonyl.

4. The diether of claim 3 wherein X is alkylene and n is an average number from 1 to about 10.

5. The diether of claim 4 wherein X is 2,2-propylene and the ether has a number average molecular weight of from about 2000 to about 4000.

* * * * *